(12) United States Patent
Deng et al.

(10) Patent No.: US 12,685,536 B2
(45) Date of Patent: Jul. 21, 2026

(54) GUGLIELMI DETACHABLE COIL PUSHING ROD END STRUCTURE, AND DETACHING SYSTEM AND EMBOLIZATION SYSTEM WITH SAME

(71) Applicant: MICROPORT NEUROTECH (AMERICA) INC., Irvine, CA (US)

(72) Inventors: Shuhao Deng, Shanghai (CN); Bing Chen, Shanghai (CN); Yuanyi Guo, Shanghai (CN); Guangliang Pan, Shanghai (CN); Shuo Zhang, Shanghai (CN)

(73) Assignee: MICROPORT NEUROTECH (AMERICA) INC., Irvine, CA (US)

( * ) Notice: Subject to any disclaimer, the term of this patent is extended or adjusted under 35 U.S.C. 154(b) by 728 days.

(21) Appl. No.: 18/014,039

(22) PCT Filed: Aug. 4, 2021

(86) PCT No.: PCT/CN2021/110686
§ 371 (c)(1),
(2) Date: Dec. 30, 2022

(87) PCT Pub. No.: WO2022/002279
PCT Pub. Date: Jan. 6, 2022

(65) Prior Publication Data
US 2023/0277188 A1 Sep. 7, 2023

(30) Foreign Application Priority Data
Jun. 30, 2020 (CN) .......................... 202010618065.8

(51) Int. Cl.
A61B 17/00 (2006.01)
A61B 17/12 (2006.01)

(52) U.S. Cl.
CPC .... *A61B 17/1214* (2013.01); *A61B 17/12113* (2013.01); *A61B 2017/00526* (2013.01);
(Continued)

(58) Field of Classification Search
CPC ........ A61B 17/12022; A61B 17/12113; A61B 17/1214; A61B 17/12145;
(Continued)

(56) References Cited

U.S. PATENT DOCUMENTS 8,202,292 B2 * 6/2012 Kellett ............. A61B 17/12145
606/200
2010/0268252 A1 10/2010 Chen et al.
(Continued)

FOREIGN PATENT DOCUMENTS

CN 102186426 A 9/2011
CN 107334506 A 11/2017
(Continued)

*Primary Examiner* — Tan-Uyen T Ho
*Assistant Examiner* — Lindsey R. Rivers
(74) *Attorney, Agent, or Firm* — MUNCY, GEISSLER, OLDS & LOWE, P.C.

(57) ABSTRACT

An end structure of a push rod for a guglielmi detachable coil, detachment systems thereof, and an embolization system are disclosed. The end structure includes at least one metal wire, at least one first conductive tube, at least one insulator and at least one second conductive tube. The at least one insulator is connected to both the first conductive tube and the second conductive tube and configured to electrically insulate the first conductive tube from the second conductive tube. One end of the at least one metal wire is electrically connected to the at least one second conductive tube. The first conductive tube and the second conductive tube are coaxially assembled into an integral structure, which can be inserted into an electrolytic device, resulting in the formation of an electrical circuit.

18 Claims, 5 Drawing Sheets

(52) U.S. Cl.
CPC ............... *A61B 2017/00929* (2013.01); *A61B 2017/12063* (2013.01)

(58) Field of Classification Search
CPC ........... A61B 2017/00526; A61B 2017/00831; A61B 2017/0092; A61B 2017/00929; A61B 2017/12063
See application file for complete search history.

(56) References Cited

U.S. PATENT DOCUMENTS

2011/0106098 A1 * 5/2011 Williams ......... A61B 17/12154
606/108
2019/0175199 A1 6/2019 Girdhar et al.

FOREIGN PATENT DOCUMENTS

| CN | 212913299 U | | 4/2021 | | |
|----|-------------|---|--------|---|---|
| EP | 1443873 B1 | * | 3/2007 | ....... | A61B 17/12113 |
| WO | WO-9512367 A1 | * | 5/1995 | ....... | A61B 17/12113 |
| WO | WO-9942157 A2 | * | 8/1999 | ....... | A61B 17/12181 |

* cited by examiner

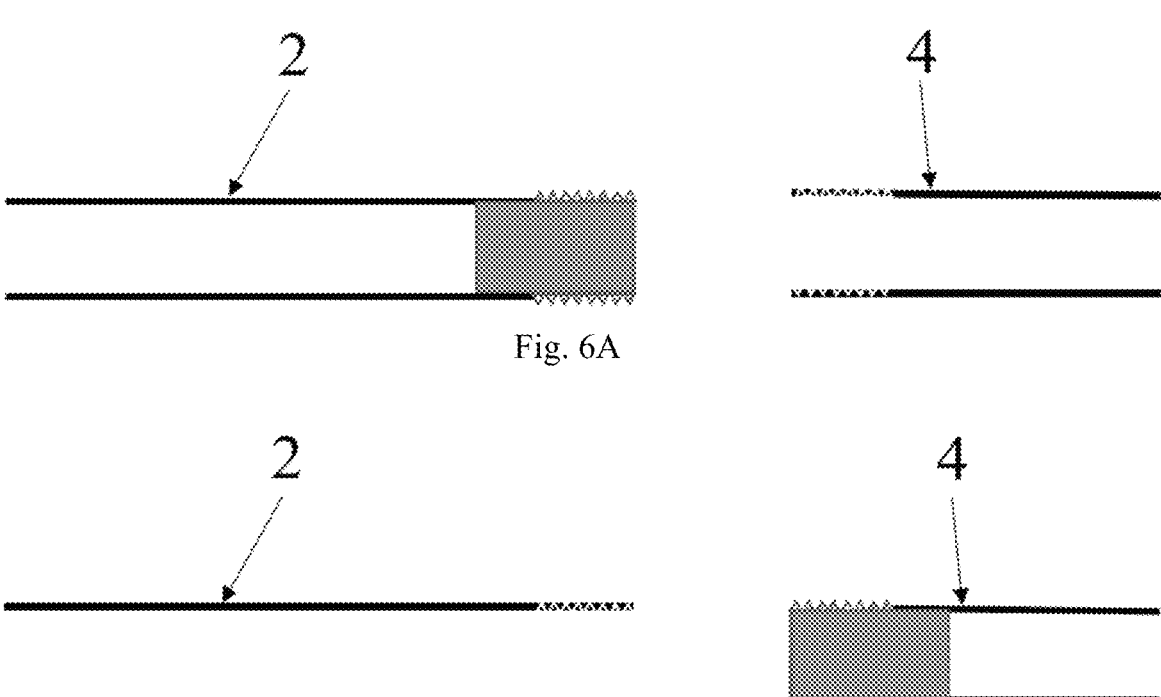
Fig. 6A
Fig. 6B
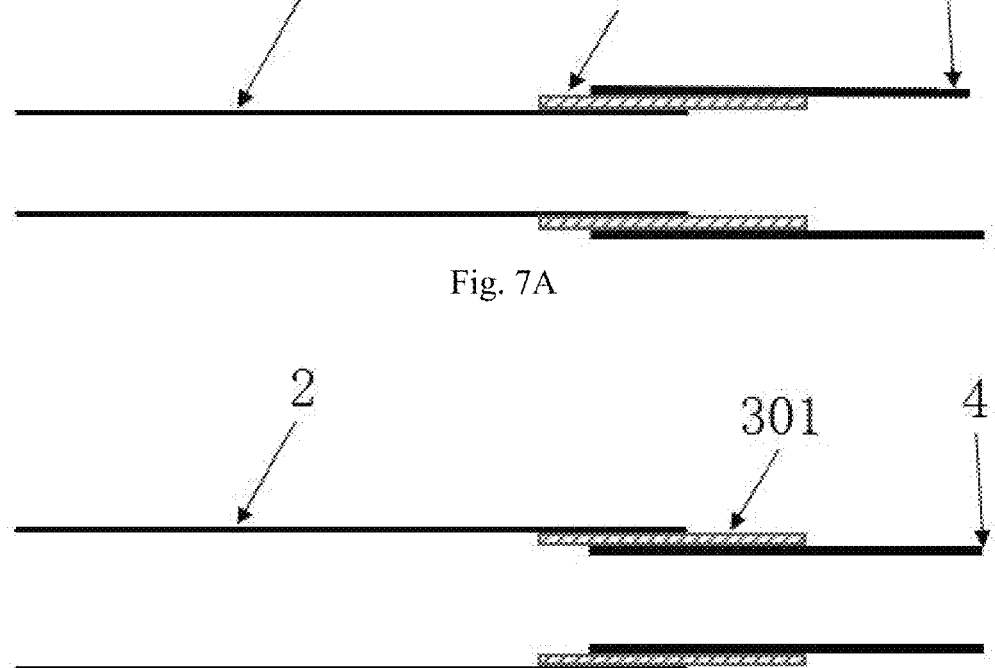
Fig. 7A
Fig. 7B

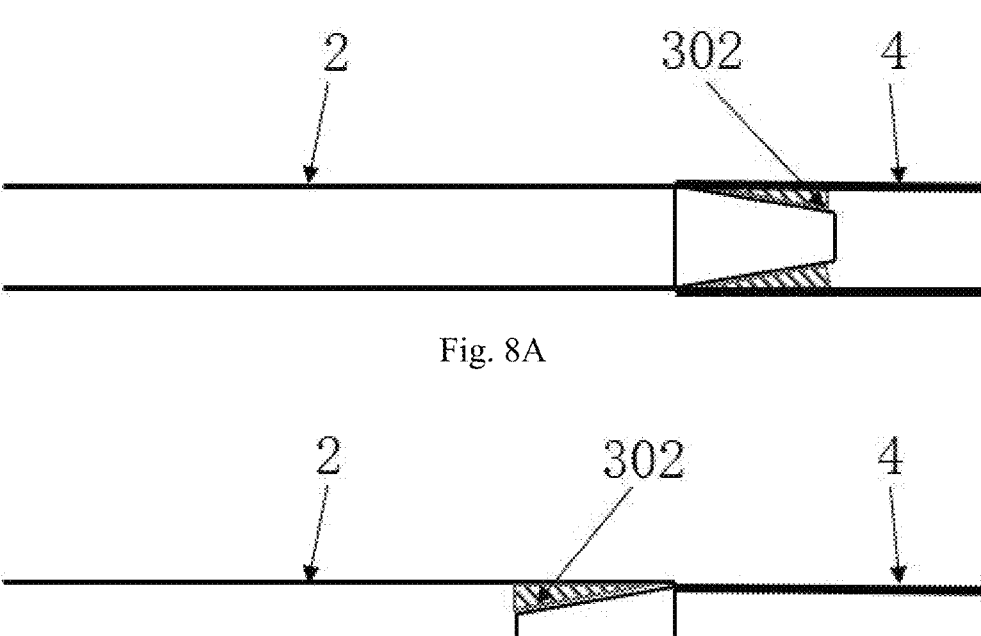
Fig. 8A
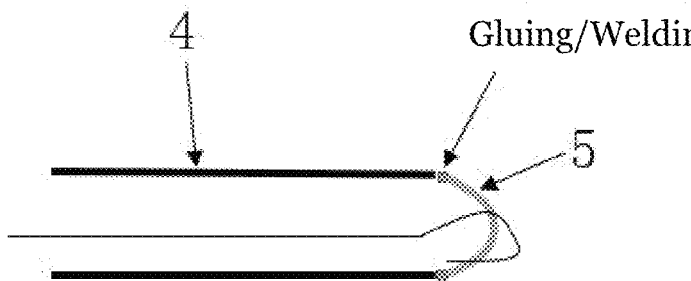
Fig. 8B
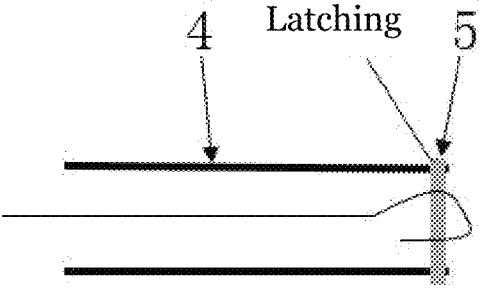
Fig. 9
Fig. 10

GUGLIELMI DETACHABLE COIL PUSHING ROD END STRUCTURE, AND DETACHING SYSTEM AND EMBOLIZATION SYSTEM WITH SAME

TECHNICAL FIELD

The present invention relates to the field of medical instruments and, in particular, to an end structure of a push rod for a guglielmi detachable coil, detachment systems thereof and an embolization system.

BACKGROUND

In recent years, intracranial aneurysms have been more and more prevalent and become a common disease. This disease must not be underestimated due to its high mortality and disability. There are two therapies for intracranial aneurysms, i.e., surgical clipping and endovascular intervention. In contrast to the surgical approach that is associated with a high risk of aneurysmal rupture, the interventional approach provides a variety of advantages including less invasiveness, lower risk and fewer complications and is therefore receiving increasing attention and importance.

Interventional treatment of an aneurysm is essentially based on a coil embolization technique involving implanting a coil into the aneurysm, which can disturb blood flow and facilitate the formation of a dense embolus, thereby providing a therapeutic effect on the intracranial aneurysm. The implantation of the coil requires the use of a delivery system (push rod) for advancing the coil to the aneurysmal site, where the coil is then detached from the delivery system, followed by withdrawal of the delivery system (push rod).

The Guglielmi detachable coil (GDC), a traditional product for interventional treatment of aneurysms, employs electrolytic detachment. A positive terminal in an end structure of a push rod for the guglielmi detachable coil is connected to a bare metal section of a guide wire on which the coil is to be delivered, while a negative terminal is connected to a steel needle subcutaneously inserted into a patient. The end structure is then energized, and an electrical circuit is formed through the human body. As a result, the bare metal section of the guide wire to which the positive terminal is connected is melted, resulting in detachment. Although this electrolytic detachment method is robust and reliable, it requires complicated operation and takes a long time to achieve detachment. Moreover, the subcutaneous insertion of the needle would cause additional trauma and pain to the patient.

SUMMARY OF THE INVENTION

In view of the above-discussed shortcomings of the prior art, it is an objective of the present invention to provide an end structure of a push rod for a guglielmi detachable coil, detachment systems thereof and an embolization system. The present invention is advantageous over the conventional guglielmi detachable coil by dispensing with the need to insert a needle into a patient, which would cause additional pain to the patient, and by involving simplified operation of a physician.

To this end, the present invention provides an end structure of a push rod for a guglielmi detachable coil, which comprises at least one metal wire, at least one first conductive tube, at least one insulator and at least one second conductive tube.

The at least one insulator is connected to both the first conductive tube and the second conductive tube and configured to electrically insulate the first conductive tube from the second conductive tube. The first conductive tube and the second conductive tube are assembled coaxially.

The at least one metal wire is electrically connected at one end to the at least one second conductive tube.

Optionally, the end structure may further comprise at least one stopper, wherein one end of the at least one metal wire is connected to the at least one stopper.

Optionally, the end structure may further comprise at least one securing member formed at one end of the second conductive tube, wherein the at least one securing member is connected to one end of the at least one metal wire.

Optionally, the metal wire may have a proximal section, a distal section and an intermediate section between the proximal section and the distal section.

Optionally, the metal wire may be made of a material selected from one or more of silver, copper, platinum and stainless steel.

Optionally, the metal wire may have a diameter in the range of 0.04-0.08 mm and a length in the range of 1600-2400 mm.

Optionally, the proximal section of the metal wire may be disposed in a lumen of the second conductive tube, the intermediate section of the metal wire in a lumen of the first conductive tube, and the distal section of the metal wire outside of the lumens of the tubes.

Optionally, at least part of the proximal section of the metal wire may form a first bare wire segment, which is not covered with an insulating coating and brought into contact with both the stopper and the securing member and has a length in the range of 10-50 mm.

Optionally, the intermediate section of the metal wire may be covered with an insulating coating and have a length in the range of 1550-2200 mm.

Optionally, the distal section of the metal wire may have a length in the range of 50-200 mm.

Optionally, the distal section of the metal wire may have a second bare wire segment, which is not covered with an insulating coating and serves as a detachable feature for forming a detachment circuit with the first conductive tube in an electrolytic environment, wherein the detachable feature has a length in the range of 0.01-0.08 mm.

Optionally, each of the first conductive tube and the second conductive tube may be fabricated from a metal tube.

Optionally, each of the first conductive tube and the second conductive tube may have an outer diameter in the range of 0.30-0.45 mm and an inner diameter in the range of 0.15-0.35 mm.

Optionally, the first conductive tube may have a length in the range of 1400-2000 mm and the second conductive tube may have a length in the range of 200-400 mm.

Optionally, the first conductive tube and the second conductive tube may be directly connected to each other, with the insulator being disposed at a joint of the first conductive tube and the second conductive tube.

Optionally, the first conductive tube and the second conductive tube may be nested together.

Optionally, the first conductive tube or the second conductive tube may therefore have at least one nested end portion. The at least one nested end portion may have a length in the range of 10-40 mm.

Optionally, the insulator may be implemented as a heat-shrinkable insulating tube or formed of an insulating material.

Optionally, one end of the heat-shrinkable insulating tube may be fitted over an outer circumference of an end portion of the first conductive tube, whilst the other end of the heat-shrinkable insulating tube may fit within an inner circumference of an end portion of the second conductive tube. Alternatively, one end of the heat-shrinkable insulating tube may be fitted over an outer circumference of an end portion of the second conductive tube, whilst the other end of the heat-shrinkable insulating tube may fit within an inner circumference of an end portion of the first conductive tube.

Optionally, the insulating material may be spray coated on the joint of the first and second conductive tubes.

Optionally, the insulating material may be selected from any of a polyimide coating, an alumina ceramic coating, a ceramic polymer coating, a polybenzimidazole coating and a polytetrafluoroethylene coating.

Optionally, the first conductive tube and the second conductive tube may be indirectly connected to each other by the insulator.

Optionally, the insulator may be implemented as a sleeve connecting the first conductive tube to the second conductive tube.

Optionally, the sleeve may cover outer circumferences of joint portions of the first conductive tube and the second conductive tube, which abut against each other or together form a lap joint.

Optionally, the sleeve may have a length in the range of 20-60 mm and a thickness in the range of 0.05-0.1 mm.

Optionally, the insulator may be implemented as a plunger tube connecting the first conductive tube to the second conductive tube.

Optionally, the plunger tube may have a length in the range of 20-60 mm and a thickness in the range of 0.1-0.15 mm.

Optionally, the insulator may be implemented as a plug and socket assembly connecting the first conductive tube to the second conductive tube or threadedly couple the first conductive tube to the second conductive tube.

Optionally, the at least one stopper may be implemented as any of a circular ring, a circular tube, a square tube, a perforated circular tube, a perforated square tube and a perforated ball. Additionally or alternatively, the stopper may be made of a material selected from one or more of gold, silver, copper, a platinum-gold alloy, a platinum-tungsten alloy and a platinum-iridium alloy.

Optionally, the at least one stopper may be disposed inside the second conductive tube, or so that its end face is coplanar and flush with an end face of the second conductive tube, or outside of an end of the second conductive tube.

Optionally, the at least one stopper may be disposed outside of the end of the second conductive tube at a distance in the range of 0-2 mm therefrom.

Optionally, the at least one stopper may be connected to the second conductive tube by gluing, welding or latching.

Optionally, one end of the securing member may extend into a lumen of the second conductive tube so as to wrap around one end of each of the stopper and the metal wire.

Optionally, the securing member may be made of a conductive adhesive material.

Optionally, the conductive adhesive material may cure so as to assume the shape of a hemisphere or ellipsoid.

Optionally, the hemisphere may have a radius in the range of 0.3-0.45 mm.

Optionally, an apex of the ellipsoid may be spaced from an end of the second conductive tube by a distance in the range of 0.15-0.65 mm.

A detachment system comprising the end structure as defined above further comprises a detacher comprising a positive power supply terminal and a negative power supply terminal, in which:

the negative power supply terminal forms a negative circuit portion together with the first conductive tube;

the positive power supply terminal forms a positive circuit portion together with the second conductive tube and the metal wire; and the distal section of the metal wire comprises a detachable feature, which, when situated in an electrolytic environment together with the first conductive tube, an electrical connection is established between the negative circuit portion and the positive circuit portion so that the two portions form a detachment circuit.

Optionally, the detacher may provide a DC or AC current.

Another detachment system comprising the end structure as defined above further comprises a detacher comprising a positive power supply terminal and a negative power supply terminal, in which:

the positive power supply terminal forms a positive circuit portion together with the first conductive tube;

the negative power supply terminal forms a negative circuit portion together with the second conductive tube and the metal wire; and the distal section of the metal wire comprises a detachable feature, which, when situated in an electrolytic environment together with the first conductive tube, an electrical connection is established between the negative circuit portion and the positive circuit portion so that the two portions form a detachment circuit.

Optionally, the detacher may provide a DC or AC current.

An embolization system comprising the end structure as defined above further comprises a metal or degradable coil.

Optionally, the metal or degradable coil may comprise a 2D primary structure or a 3D secondary structure.

Optionally, the degradable coil may be made of a material selected from any of a polymer coating, a hydrophilic coating and a bioactive material coating.

Optionally, the degradable coil may comprise at least one first coil portion and at least one second coil portion.

Optionally, the at least one first coil portion and the at least one second coil portion may be coaxially arranged in such a manner that the at least one second coil portion is located within a cavity defined by the at least one first coil portion.

Optionally, the at least one first coil portion may be made of a polymer material, such as any of polylactic acid, polyglycolic acid, poly(lactic acid-co-glycolic acid), poly-4-dioxan-2-one, polycaprolactone, polyurethane, chitosan and hyaluronic acid.

Optionally, the at least one first coil portion may be made of a metallic material, which is any of magnesium and alloys thereof and iron and alloys thereof.

Optionally, the at least one second coil portion may be radiopaque.

Optionally, the at least one second coil portion may have a length that is not greater than a length of the at least one first coil portion.

Compared with the prior art, the present invention provides the following beneficial effects:

(1) Through separating the first and second conductive tubes by the insulator disposed therebetween, the risk of a short circuit can be effectively avoided. The first and second conductive tubes may be coaxially connected together into an integral structure by any of mutual nesting, a sleeve, a plunger tube, a plug and socket assembly and threads. When the integral structure is inserted into an electrolytic device, a detachment circuit can be formed to enable detachment.

(2) The stopper enables the metal wire to be hooked on and thus electrically connected to the second conductive tube of the push rod. Moreover, the conductive securing member provided on the second conductive tube can not only secure the metal wire and prevent its displacement, but also enables an increased contact area between the metal wire and the second conductive tube, avoiding the risk of an open circuit.

According to the present invention, the first conductive tube and the second conductive tube are coaxially assembled into an integral structure, which can be inserted into an electrolytic device, resulting in the formation of an electrical circuit. In this way, operation to be performed by a physician can be simplified, and a coil can be detached within a short period of time, resulting in increased surgical efficiency. Moreover, insertion of a needle into a patient's body as required by conventional electrolytic detachment techniques is dispensed with, reducing trauma and pain caused to the patient.

BRIEF DESCRIPTION OF THE DRAWINGS

FIG. 6A schematically illustrates a positive terminal member and a negative terminal member, which are assembled threadedly by means of an external thread on the positive terminal member and an internal thread on the negative terminal member, in an end structure of a push rod for a guglielmi detachable coil according to an embodiment of the present invention.

FIG. 6B schematically illustrates a positive terminal member and a negative terminal member, which are assembled threadedly by means of an internal thread on the positive terminal member and an external thread on the negative terminal member, in an end structure of a push rod for a guglielmi detachable coil according to an embodiment of the present invention.

FIG. 7A schematically illustrates a heat-shrinkable insulating tube fitted over a negative terminal member in an end structure of a push rod for a guglielmi detachable coil according to an embodiment of the present invention.

FIG. 7B schematically illustrates a heat-shrinkable insulating tube fitted over a positive terminal member in an end structure of a push rod for a guglielmi detachable coil according to an embodiment of the present invention.

FIG. 8A schematically illustrates an insulating coating applied over a negative terminal member in an end structure of a push rod for a guglielmi detachable coil according to an embodiment of the present invention.

FIG. 8B schematically illustrates an insulating coating applied over a positive terminal member in an end structure of a push rod for a guglielmi detachable coil according to an embodiment of the present invention.

FIG. 9 schematically illustrates a stopper glued or welded to a positive terminal member in an end structure of a push rod for a guglielmi detachable coil according to an embodiment of the present invention.

FIG. 10 schematically illustrates a stopper connected to a positive terminal member by latching in an end structure of a push rod for a guglielmi detachable coil according to an embodiment of the present invention.

In these figures: 1—metal wire; 2—first conductive tube; 3—insulator; 301—heat-shrinkable insulating tube; 302—insulating material; 4—second conductive tube; 5—stopper; 6—securing member; 7—detachable feature; 8—nested end portion; 9—sleeve; 10—plunger tube.

DETAILED DESCRIPTION

Objectives, advantages and features of the present invention will become more apparent from the following detailed description of embodiments thereof, which is to be read in conjunction with the accompanying drawings. It will be understood that the specific embodiments are presented herein merely for the purpose of illustration rather than limitation.

In the description herein, it would be appreciated that the orientational or positional relationships described by the terms "central", "lateral", "upper", "lower", "left", "right", "vertical", "horizontal", "top", "bottom", "inner", "outer", etc. are based on the orientations or positions shown in the accompanying drawings. They are intended merely to facilitate and simplify the explanation of the application and do not indicate or imply that the stated components or elements have to assume, or be constructed or operated in, particular orientations. Therefore, they are not to be construed as limiting the application.

As used hereinabove, the terms "proximal" and "distal" describe relative orientations, relative positions and directions between elements or actions, as viewed by a physician who is operating a product. Without wishing to be limiting, a "proximal section" usually refers to an end closer to the physician, and a "distal section" usually refers to an end that enters the patient first, during normal operation of the product.

Figure 1:
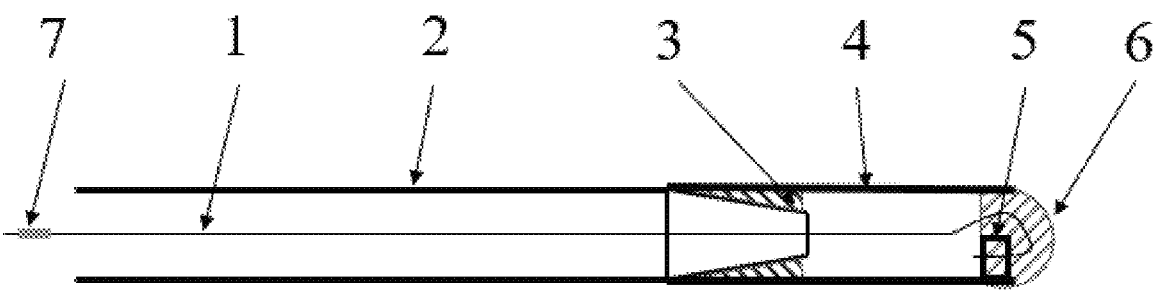
FIG. 1 schematically illustrates an end structure of a push rod for a guglielmi detachable coil according to an embodiment of the present invention.

Reference is first made to FIG. 1, a schematic illustration of an end structure of a push rod for a guglielmi detachable coil according to an embodiment of the present invention. The end structure includes at least one metal wire 1, at least one first conductive tube 2, at least one insulator 3 and at least one second conductive tube 4. The at least one insulator 3 is connected to both the first conductive tube 2 and the second conductive tube 4 and is configured to insulate the first conductive tube 2 from the second conductive tube 4. The at least one metal wire 1 is electrically connected at one end to the at least one second conductive tube 4.

In a first embodiment, the first conductive tube 2 provides a negative terminal, and the second conductive tube 4 provides a positive terminal. One end of the metal wire 1 is passed through a hollow lumen and hooked on a stopper 5. An end portion of the second conductive tube 4 defines a securing member 6, the securing member 6 secures the connection between the metal wire 1 and the second conductive tube 4 to avoid insufficient contact and ensure electrical connection between the second conductive tube 4 and the metal wire 1. The first conductive tube 2, the second conductive tube 4, the metal wire 1 and the insulator 3 are assembled together, and the assembly is inserted into a detachment device which, when energized, can form therein an electrical circuit capable of achieving detachment in a convenient, fast and effective away. In some other embodiments, the first conductive tube 2 may provide a positive terminal, while the second conductive tube 4 may provide a negative terminal.

The metal wire 1 is provided by a metal wire with good electrical conductivity. In the first embodiment, the metal wire 1 is made of stainless steels. Possible materials for the metal wire may include, but are not limited to, one or more of gold, silver, copper, platinum and stainless steel. As shown in FIG. 1, according to an embodiment of the present invention, the metal wire 1 in the end structure is generally divided into three sections located at three locations. Specifically, the metal wire 1 may have a proximal section, a distal section and an intermediate section between the proximal and distal sections. The proximal section of the metal wire 1 may be received in a lumen of the second conductive tube 4. The intermediate section of the metal wire 1 may be received in a lumen of the first conductive tube 2. The distal section of the metal wire 1 may be located outside of the lumens of the tubes. The present invention is not limited to any locations of the three sections of the metal wire 1, as long as the second conductive tube 4 can be energized.

The proximal section of the metal wire 1 may be a first bare wire segment, which is not covered with an insulating coating and brought into contact with both the stopper 5 and the securing member 6. The first bare wire segment may have a length in the range of 0.1-1 mm. Preferably, in the first embodiment, the length of the first bare wire segment is in the range of 0.3-0.5 mm.

The intermediate section of the metal wire 1 may be covered with an insulating coating and may have a length in the range of 1550-2200 mm. The distal section of the metal wire 1 may have a length in the range of 10-30 mm. Preferably, in the first embodiment, the length of the intermediate section of the metal wire 1 is in the range of 1800-1900 mm, and the length of the distal section of the metal wire 1 is in the range of 15-25 mm.

The distal section of the metal wire 1 may have a second bare wire segment not covered with an insulating coating. The second bare wire segment is provided as a detachable feature 7, which can form a detachment circuit with the first conductive tube 2 in an electrolytic environment (e.g., a body fluid environment). The detachable feature 7 may have a length in the range of 0.01-0.08 mm. Preferably, in the first embodiment, the length of the detachable feature 7 preferably lies between 0.025 mm and 0.06 mm.

The metal wire 1 may have a diameter in the range of 0.04-0.08 mm and a length in the range of 1600-2400 mm. Preferably, in the first embodiment, the diameter of the metal wire 1 is preferred to range from 0.04 mm to 0.06 mm, and the length thereof is preferred to range from 1800 mm to 1900 mm.

How the first conductive tube 2 and the second conductive tube 4 in the end structure are structured and connected in accordance with an embodiment of the present invention will be described in detail below.

Figure 2A:
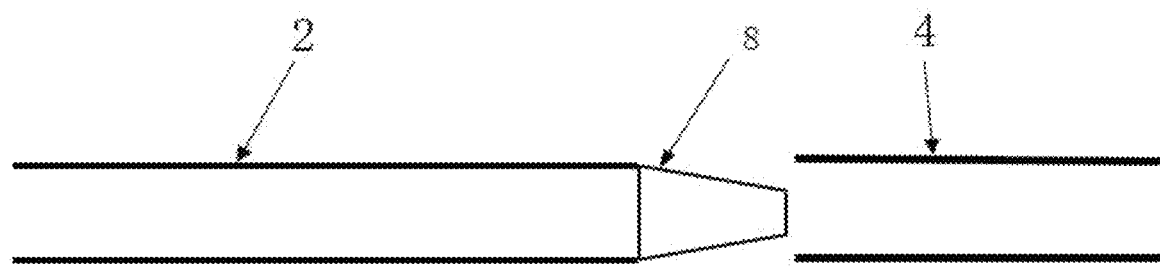
FIG. 2A schematically illustrates a negative terminal member nested in a positive terminal member in an end structure of a push rod for a guglielmi detachable coil according to an embodiment of the present invention.
Figure 2B:
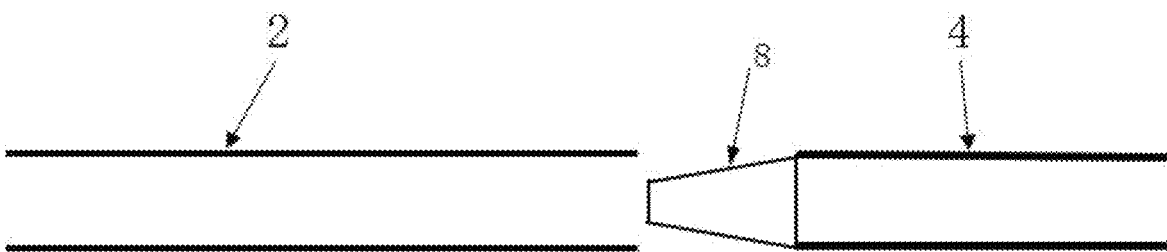
FIG. 2B schematically illustrates a positive terminal member nested in a negative terminal member in an end structure of a push rod for a guglielmi detachable coil according to an embodiment of the present invention.

The first conductive tube 2 and the second conductive tube 4 may be directly connected together, as shown in FIG. 1, 2A or 2B, the insulator 3 is arranged at the joint of the first conductive tube 2 and the second conductive tube 4. Specifically, in FIG. 1, 2A or 2B, the direct connection between the first conductive tube 2 and the second conductive tube 4 may be accomplished by nesting. Accordingly, the first conductive tube 2 or the second conductive tube 4 may have at least one nested end portion 8 having a length in the range of 10-40 mm. The nested end portion 8 may have a diameter gradually decreasing from a trailing end to a leading end thereof. As shown in FIG. 2A, the nested end portion 8 may be provided by the first conductive tube 2, and the first conductive tube 2 may be nested into the second conductive tube 4 through the nested end portion 8. As shown in FIG. 2B, the nested end portion 8 may be alternatively provided by the second conductive tube 4. In this case, the second conductive tube 4 can be nested in the first conductive tube 2 by means of the nested end portion 8. In the first embodiment, the first conductive tube 2 is nested in the second conductive tube 4, as shown in FIG. 2A. Preferably, in this nesting method, the length of the nested end portion 8 preferably ranges from 15 mm to 20 mm. In some embodiments, the nested end portion 8 may be obtained by machining a corresponding end portion of the first conductive tube 2 or the second conductive tube 4.

Next, the insulator 3 in the above nesting methods will be detailed.

As shown in FIGS. 7A, 7B, 8A and 8B, the insulator 3 may be provided in the form of a heat-shrinkable insulating tube 301, or may be made of an insulating material 302. The insulator 3 is configured to connect the first conductive tube 2 to the second conductive tube 4 in such a manner that the first conductive tube 2 is insulated from the second conductive tube 4, avoiding the occurrence of a short circuit.

As shown in FIG. 7A, in the case of a heat-shrinkable insulating tube 301, one end of the heat-shrinkable insulating tube 301 may be fitted over an outer circumference of an end portion of the first conductive tube 2, and the other end of the heat-shrinkable insulating tube 301 may fit within an inner circumference of an end portion of the second conductive tube 4. Alternatively, as shown in FIG. 7B, one end of the heat-shrinkable insulating tube 301 may be fitted over an outer circumference of an end portion of the second conductive tube 4, and the other end of the heat-shrinkable insulating tube 301 may fit within an inner circumference of an end portion of the first conductive tube 2. In some embodiments, the heat-shrinkable insulating tube 301 may be a heat-shrinkable PET tube.

As shown in FIGS. 8A and 8B, in the case of the insulator being made of an insulating material 302, the insulating material 302 may be spray coated on the joint of the first conductive tube 2 and the second conductive tube 4. The insulating material 302 may be any one of a polyimide coating, an alumina ceramic coating, a ceramic polymer coating, a polybenzimidazole coating and a polytetrafluoroethylene coating.

Alternatively, the first conductive tube 2 and the second conductive tube 4 may be connected together indirectly by the insulator 3.

Figure 3A:
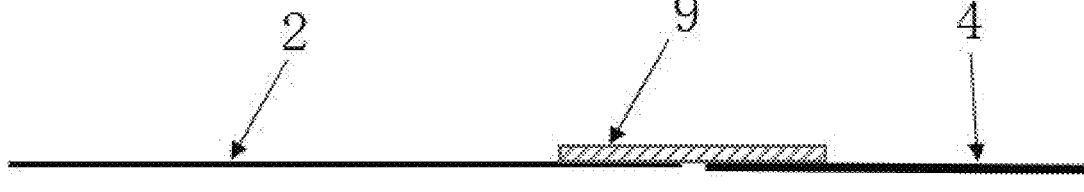
FIG. 3A schematically illustrates a positive terminal member and a negative terminal member, which are assembled by a sleeve in such a manner that they abut against each other, in an end structure of a push rod for a guglielmi detachable coil according to an embodiment of the present invention.
Figure 3B:
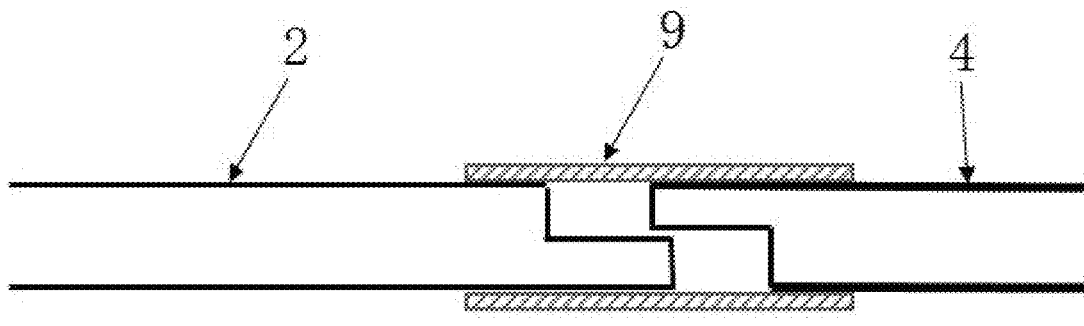
FIG. 3B schematically illustrates a positive terminal member and a negative terminal member, which are assembled by a sleeve in such a manner that they form a lap joint, in an end structure of a push rod for a guglielmi detachable coil according to an embodiment of the present invention.

Optionally, the insulator 3 may be implemented as a sleeve 9 connecting the first conductive tube 2 to the second conductive tube 4. The sleeve 9 may be fitted over outer circumferences of joint portions of the first conductive tube 2 and second conductive tube 4. As shown in FIG. 3A, the joint portions of the first conductive tube 2 and second conductive tube 4 may abut against each other. As shown in FIG. 3B, the joint portions of the first conductive tube 2 and second conductive tube 4 may form a lap joint. The sleeve 9 may have a length in the range of 5-30 mm and a thickness in the range of 0.005-0.1 mm.

Figure 4:
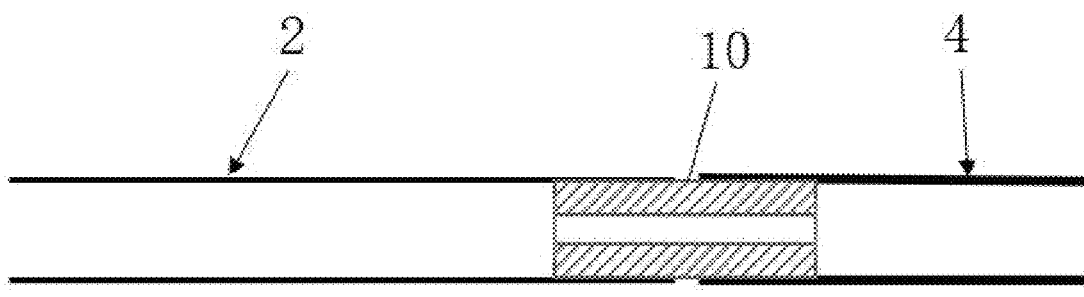
FIG. 4 schematically illustrates a positive terminal member and a negative terminal member, which are assembled by a plunger tube, in an end structure of a push rod for a guglielmi detachable coil according to an embodiment of the present invention.

Optionally, as shown in FIG. 4, the insulator 3 may be implemented as a plunger tube 10 which indirectly connects the first conductive tube 2 to the second conductive tube 4. Opposing end portions of the plunger tube 10 may fit within inner circumferences of ends portions of the first conductive tube 2 and the second conductive tube 4. The plunger tube 10 may have a length in the range of 5-30 mm and a thickness in the range of 0.1-0.15 mm.

Figure 5A:
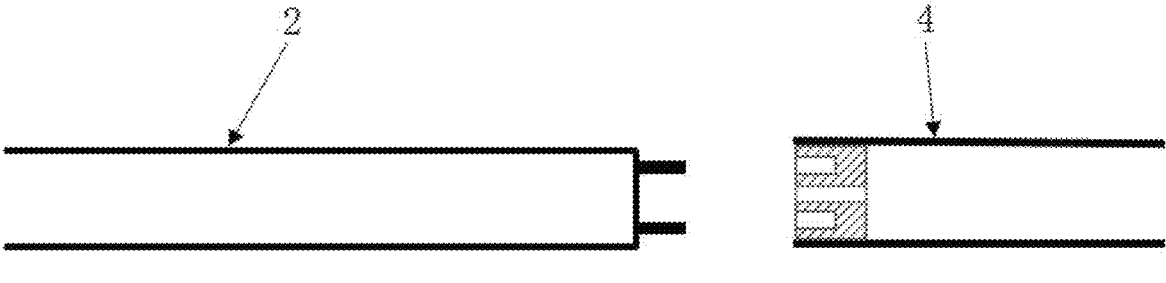
FIG. 5A schematically illustrates a positive terminal member and a negative terminal member, which form a plug and socket assembly and are assembled in such a manner that the positive terminal member inserted in the negative terminal member, in an end structure of a push rod for a guglielmi detachable coil according to an embodiment of the present invention.
Figure 5B:
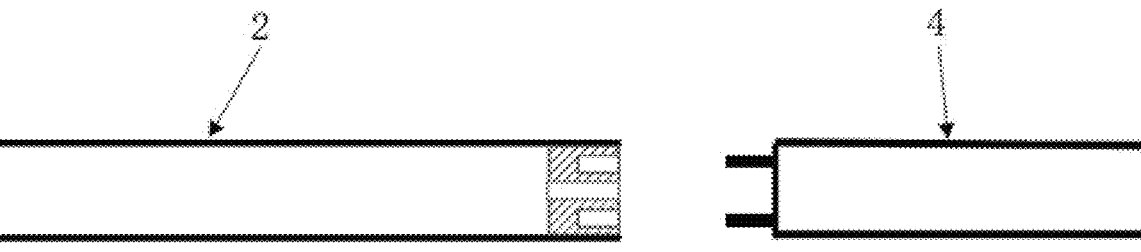
FIG. 5B schematically illustrates a positive terminal member and a negative terminal member, which form a plug and socket assembly and are assembled in such a manner that the negative terminal member inserted in the positive terminal member, in an end structure of a push rod for a guglielmi detachable coil according to an embodiment of the present invention.

Optionally, the insulator 3 may be implemented as a plug and socket assembly connecting the first conductive tube 2 to the second conductive tube 4. As shown in FIG. 5A, the first conductive tube 2 may be provided at one end with a plug sub-assembly, and the second conductive tube 4 may be provided at one end with a socket sub-assembly. Alternatively, as shown in FIG. 5B, the first conductive tube 2 may be provided at one end with a socket sub-assembly, and the second conductive tube 4 may be provided at one end with a plug sub-assembly.

Optionally, the insulator 3 may accomplish the connection of the first conductive tube 2 and the second conductive tube 4 threadedly. As shown in FIG. 6A, the first conductive tube 2 may be provided at one end with an external thread, and the second conductive tube 4 may be provided at one end with an internal thread. Alternatively, as shown in FIG. 6B, the first conductive tube 2 may be provided at one end with an internal thread, and the second conductive tube 4 may be provided at one end with an external thread.

Each of the first conductive tube 2 and the second conductive tube 4 may be fabricated from a metal tube. Each of the first conductive tube 2 and the second conductive tube 4 may have an outer diameter in the range of 0.30-0.45 mm and an inner diameter in the range of 0.15-0.35 mm. The first conductive tube 2 may have a length in the range of 1400-2000 mm, and the second conductive tube 4 may have a length in the range of 200-400 mm.

The stopper 5 in the end structure according to an embodiment of the present invention will be detailed below.

The stopper 5 is provided to enable the first bare wire segment of the proximal section of the metal wire 1 to be hooked on and electrically connected to the second conductive tube 4. The stopper 5 may be implemented as any of a circular ring, a circular tube, a square tube, a perforated circular tube, a perforated square tube and a perforated ball. Possible materials for it may include, but are not limited to, gold, silver, copper, platinum-gold alloy, a platinum-tungsten alloy, a platinum-iridium alloy, etc. Preferably, in this embodiment, the stopper 5 is a circular ring. The stopper 5 may be disposed at any of the following locations with respect to the second conductive tube 4.

Location 1:

The stopper 5 is disposed inside the second conductive tube 4.

Location 2:

The stopper 5 is disposed with its one end face being flush with an end face of the second conductive tube 4. In this embodiment, the stopper 5 is disposed at Location 2.

Location 3:

The stopper 5 is disposed outside of an end of the second conductive tube 4. The stopper 5 may be disposed at a distance in the range of 0-2 mm from the end of the second conductive tube 4. Preferably, the distance of the stopper 5 from the end of the second conductive tube 4 ranges from 0.1 mm to 0.5 mm.

As shown in FIGS. 9 and 10, at the above three locations, methods for connecting the stopper 5 to the second conductive tube 4 may include, but are not limited to, gluing, welding and latching. In this embodiment, the stopper 5 is connected to the second conductive tube 4 by welding.

Next, the securing member 6 in the end structure according to an embodiment of the present invention will be detailed below.

Figure 11:
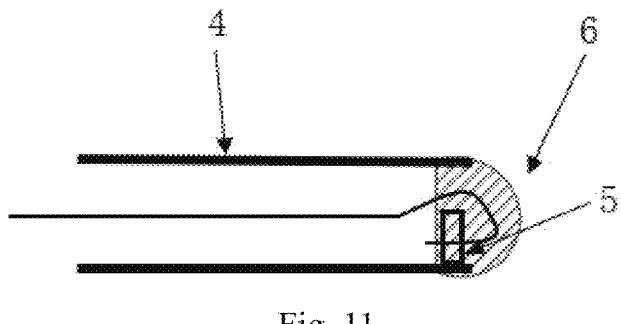
FIG. 11 schematically illustrates a hemispherical securing member in an end structure of a push rod for a guglielmi detachable coil according to an embodiment of the present invention.
Figure 12A:
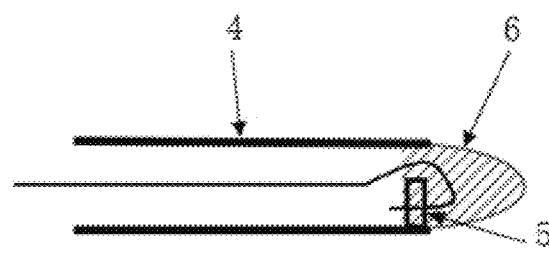
FIG. 12A schematically illustrates a securing member, which is an ellipsoid with a larger area, in an end structure of a push rod for a guglielmi detachable coil according to an embodiment of the present invention.
Figure 12B:
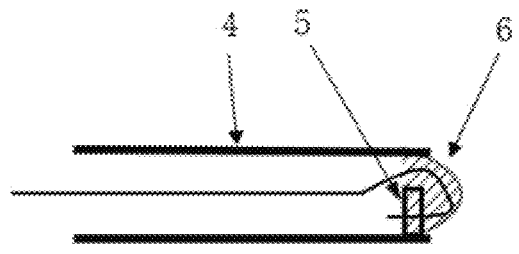
FIG. 12B schematically illustrates a securing member, which is an ellipsoid with a smaller area, in an end structure of a push rod for a guglielmi detachable coil according to an embodiment of the present invention.

As shown in FIGS. 11, 12A and 12B, one end of the securing member 6 extends into the lumen of the second conductive tube 4 so as to wrap around an end portion of each of the stopper 5 and the metal wire 1. The securing member 6 may be made of a conductive adhesive material. In the first embodiment, the conductive adhesive material is implemented as conductive glue, which cures so as to assume the shape of a hemisphere or ellipsoid. Preferably, in this embodiment, the conductive glue cures so as to have an ellipsoid shape. The hemisphere may have a radius in the range of 0.29-0.32 mm. As shown in FIGS. 12A and 12B, an apex of the ellipsoid may be spaced from the end of the second conductive tube 4 by a distance in the range of 0.15-0.65 mm. In this embodiment, preferably, the distance from the apex of the ellipsoid to the end of the second conductive tube 4 ranges from 0.15 mm to 0.25 mm.

In another embodiment of the present invention, there is provided a detachment system including the end structure as defined above. The detachment system further includes a detacher for providing a DC or AC current. The detacher includes a positive power supply terminal and a negative power supply terminal.

The negative power supply terminal and the first conductive tube form a negative circuit portion.

The positive power supply terminal, the second conductive tube and the metal wire form a positive circuit portion.

The distal section of the metal wire includes a detachable feature. When this detachable feature and the first conductive tube are both situated in an electrolytic environment, an electrical connection is established between the negative and positive circuit portions and the two portions thus form a detachment circuit.

In yet another embodiment of the present invention, there is provided another detachment system including the end structure as defined above. The embolization system further includes a detacher for providing a DC or AC current. The detacher includes a positive power supply terminal and a negative power supply terminal.

The positive power supply terminal and the first conductive tube form a positive circuit portion.

The negative power supply terminal, the second conductive tube and the metal wire form a negative circuit portion.

The distal section of the metal wire includes a detachable feature. When this detachable feature and the first conductive tube are both situated in an electrolytic environment, an electrical connection is established between the negative and positive circuit portions and the two portions thus form a detachment circuit.

In still another embodiment of the present invention, there is provided an embolization system including a push rod with the end structure as defined above and a coil. The coil may be either a metal coil or a degradable coil.

Preferably, in the case of the coil being implemented as a metal coil, the metal coil may have a 2D primary structure or a 3D secondary structure.

Preferably, in the case of the coil being implemented as a degradable coil, the degradable coil may have a primary structure or a 3D secondary structure.

Preferably, in the case of the coil being implemented as a degradable coil, the degradable coil may be formed of any of a polymer coating, a hydrophilic coating and a bioactive material coating.

Both the metal and degradable coils may include first coil portion(s) and second coil portion(s). The first and second coil portions may be arranged coaxially. The second coil portion(s) may be disposed in a cavity defined by the first coil portion(s). The second coil portion(s) may be radiopaque. The second coil portion(s) may have a length that is less than a length of at least one of the first coil portion(s).

Preferably, the first coil portion(s) may be made of a polymer material, such as any of polylactic acid, polyglycolic acid, poly(lactic acid-co-glycolic acid), poly-4-dioxan-2-one, polycaprolactone, polyurethane, chitosan and hyaluronic acid.

Preferably, the first coil portion(s) may be alternatively made of a metallic material, which may be any of magnesium and alloys thereof and iron and alloys thereof.

The various technical features of the foregoing embodiments may be combined in any way. Although not all such combinations have been described above for the sake of brevity, any of them is considered to fall within the scope of this specification as long as there is no contradiction between the technical features.

Presented above are merely several embodiments of the present application. Although these embodiments are described with some particularity and in some detail, it should not be construed that they limit the scope of the present application in any sense. It is to be noted that various variations and modifications can be made by those of ordinary skill in the art without departing from the concept of the present application. Accordingly, it is intended that all such variations and modifications are embraced within the scope of this application as defined in the appended claims.

What is claimed is:

1. An end structure of a push rod for a guglielmi detachable coil, comprising at least one metal wire, at least one first conductive tube, at least one insulator, at least one second conductive tube, at least one stopper and at least one securing member, the at least one insulator connected to both the first conductive tube and the second conductive tube and configured to electrically insulate the first conductive tube from the second conductive tube, the first conductive tube and the second conductive tube assembled coaxially into an integral tubular structure, one end of the at least one metal wire electrically connected to the at least one second conductive tube, the metal wire having a proximal section disposed in a lumen of the second conductive tube and being hooked on the at least one stopper, wherein the integral tubular structure is configured to be inserted as a whole into a detacher, enabling the first conductive tube and the second conductive tube to respectively establish electrical connections with a positive power supply terminal and a negative power supply terminal of the detacher, wherein one end of the at least one metal wire is connected to the at least one stopper, the at least one stopper is implemented as any of a circular ring, a perforated circular tube, a perforated square tube and a perforated ball, the at least one stopper is disposed inside the second conductive tube by gluing, welding or latching, wherein the at least one securing member is formed at one end of the second conductive tube, one end of the securing member extends into the lumen of the second conductive tube so as to wrap around one end of each of the stopper and the metal wire.

2. The end structure of the push rod for the guglielmi detachable coil of claim 1, wherein the at least one securing member is connected to one end of the at least one metal wire.

3. The end structure of the push rod for the guglielmi detachable coil of claim 1, wherein the metal wire has the proximal section, a distal section and an intermediate section, the intermediate section is arranged between the proximal section and the distal section.

4. The end structure of the push rod for the guglielmi detachable coil of claim 3, wherein the metal wire is made of a material selected from one or more of silver, copper, platinum and stainless steel, the metal wire has a diameter of 0.04 mm to 0.08 mm and the metal wire has a length of 1600 mm to 2400 mm.

5. The end structure of the push rod for the guglielmi detachable coil of claim 3, wherein the intermediate section of the metal wire is disposed in a lumen of the first conductive tube, and the distal section of the metal wire is disposed outside of the lumen of the first conductive tube.

6. The end structure of the push rod for the guglielmi detachable coil of claim 5, wherein at least part of the proximal section of the metal wire forms a first bare wire segment, which is not covered with an insulating coating and brought into contact with both the stopper and the securing member, the first bare wire segment having a length in the range of 10-50 mm, and/or wherein the intermediate section of the metal wire is covered with an insulating coating and has a length in the range of 1550-2200 mm, and/or wherein the distal section of the metal wire has a length in the range of 50-200 mm.

7. The end structure of the push rod for the guglielmi detachable coil of claim 6, wherein the distal section of the metal wire has a second bare wire segment that is not covered with an insulating coating, the second bare wire segment severing as a detachable feature for forming a detachment circuit with the first conductive tube in an electrolytic environment, the detachable feature having a length in the range of 0.01-0.08 mm.

8. The end structure of the push rod for the guglielmi detachable coil of claim 1, wherein each of the first conductive tube and the second conductive tube is fabricated from a metal tube, and/or wherein each of the first conductive tube and the second conductive tube has an outer diameter in the range of 0.30-0.45 mm and an inner diameter in the range of 0.15-0.35 mm, wherein the first conductive tube has a length in the range of 1400-2000 mm and the second conductive tube has a length in the range of 200-400 mm.

9. The end structure of the push rod for the guglielmi detachable coil of claim 1, wherein the first conductive tube and the second conductive tube are directly connected to each other, the insulator being disposed at a joint of the first conductive tube and the second conductive tube; or wherein the first conductive tube and the second conductive tube are indirectly connected to each other by the insulator.

10. The end structure of the push rod for the guglielmi detachable coil of claim 1, wherein the first conductive tube and the second conductive tube are nested together and, accordingly, the first conductive tube or the second conductive tube has at least one nested end portion, the at least one nested end portion having a length in the range of 10-40 mm.

11. The end structure of the push rod for the guglielmi detachable coil of claim 1, wherein the insulator is implemented as a heat-shrinkable insulating tube, one end of the heat-shrinkable insulating tube being fitted over an outer circumference of an end portion of the first conductive tube and the other end of the heat-shrinkable insulating tube fitting within an inner circumference of an end portion of the second conductive tube, or one end of the heat-shrinkable insulating tube being fitted over an outer circumference of an end portion of the second conductive tube and the other end of the heat-shrinkable insulating tube fitting within an inner circumference of an end portion of the first conductive tube.

12. The end structure of the push rod for the guglielmi detachable coil of claim 1, wherein the insulator is implemented as a sleeve connecting the first conductive tube to the second conductive tube, the sleeve covering outer circumferences of joint portions of the first conductive tube and the second conductive tube, the joint portions of the first conductive tube and the second conductive tube abut against each other or together form a lap joint, the sleeve having a length in the range of 20-60 mm and a thickness in the range of 0.05-0.1 mm.

13. The end structure of the push rod for the guglielmi detachable coil of claim 1, wherein the at least one stopper is made of a material selected from one or more of gold, silver, copper, a platinum-gold alloy, a platinum-tungsten alloy and a platinum-iridium alloy.

14. The end structure of the push rod for the guglielmi detachable coil of claim 1, wherein the securing member is made of a conductive adhesive material, which cures so as to assume the shape of a hemisphere or ellipsoid, the hemisphere having a radius in the range of 0.3-0.45 mm, or the ellipsoid having an apex spaced from an end of the second conductive tube by a distance in the range of 0.15-0.65 mm.

15. The end structure of the push rod for the guglielmi detachable coil of claim 1, wherein the insulator is made of an insulating material, the insulating material spray coated on a joint of the first conductive tube and the second conductive tube, the insulating material selected from any one of a polyimide coating, an alumina ceramic coating, a ceramic polymer coating, a polybenzimidazole coating and a polytetrafluoroethylene coating.

16. The end structure of the push rod for the guglielmi detachable coil of claim 1, wherein the insulator is implemented as a plunger tube connecting the first conductive tube to the second conductive tube and having a length in the range of 20-60 mm and a thickness in the range of 0.1-0.15 mm, or the insulator is implemented as a plug or socket assembly connecting the first conductive tube to the second conductive tube, or threadedly couples the first conductive tube to the second conductive tube.

17. A detachment system comprising: an end structure of a push rod for a guglielmi detachable coil of, comprising at least one metal wire, at least one first conductive tube, at least one insulator, and at least one second conductive tube, at least one stopper and at least one securing member, the at least one insulator connected to both the first conductive tube and the second conductive tube and configured to electrically insulate the first conductive tube from the second conductive tube, the first conductive tube and the second conductive tube assembled coaxially into an integral tubular structure, one end of the at least one metal wire electrically connected to the at least one second conductive tube, the metal wire having a proximal section disposed in a lumen of the second conductive tube and being hooked on the at least one stopper, wherein the integral tubular structure is configured to be inserted as a whole into a detacher, enabling the first conductive tube and the second conductive tube to respectively establish electrical connections with a positive power supply terminal and a negative power supply terminal of the detacher, wherein one end of the at least one metal wire is connected to the at least one stopper, the at least one stopper is implemented as any of a circular ring, a perforated circular tube, a perforated square tube and a perforated ball, the at least one stopper is disposed inside the second conductive tube by gluing, welding or latching, wherein the at least one securing member is formed at one end of the second conductive tube, one end of the securing member extends into the lumen of the second conductive tube so as to wrap around one end of each of the stopper and the metal wire, and further comprising the detacher, the detacher comprising the positive power supply terminal and the negative power supply terminal, the negative power supply terminal forming a negative circuit portion together with the first conductive tube, the positive power supply terminal forming a positive circuit portion together with the second conductive tube and the metal wire, wherein the distal section of the metal wire comprises a detachable feature, which, when situated in an electrolytic environment together with the first conductive tube, an electrical connection is established between the negative circuit portion and the positive circuit portion so that the two portions form a detachment circuit.

18. An embolization system comprising: an end structure of a push rod for a guglielmi detachable coil, comprising at least one metal wire, at least one first conductive tube, at least one insulator, and at least one second conductive tube, at least one stopper and at least one securing member, the at least one insulator connected to both the first conductive tube and the second conductive tube and configured to electrically insulate the first conductive tube from the second conductive tube, the first conductive tube and the second conductive tube assembled coaxially into an integral tubular structure, one end of the at least one metal wire electrically connected to the at least one second conductive tube, the metal wire having a proximal section disposed in a lumen of the second conductive tube and being hooked on the at least one stopper, wherein the integral tubular structure is configured to be inserted as a whole into a detacher, enabling the first conductive tube and the second conductive tube to respectively establish electrical connections with a positive power supply terminal and a negative power supply terminal of the detacher, wherein one end of the at least one metal wire is connected to the at least one stopper, the at least one stopper is implemented as any of a circular ring, a perforated circular tube, a perforated square tube and a perforated ball, the at least one stopper is disposed inside the second conductive tube by gluing, welding or latching, wherein the at least one securing member is formed at one end of the second conductive tube, one end of the securing member extends into the lumen of the second conductive tube so as to wrap around one end of each of the stopper and the metal wire, and further comprising a metal coil or a degradable coil.

* * * * *